(12) United States Patent
Chabrol

(10) Patent No.: US 11,648,416 B2
(45) Date of Patent: May 16, 2023

(54) ILLUMINATING DEVICE IMPLANTABLE IN A LIVING BEING

(71) Applicant: COMMISSARIAT A L'ENERGIE ATOMIQUE ET AUX ENERGIES ALTERNATIVES, Paris (FR)

(72) Inventor: Claude Chabrol, Grenoble (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 50 days.

(21) Appl. No.: 17/117,318

(22) Filed: Dec. 10, 2020

(65) Prior Publication Data

US 2021/0178183 A1 Jun. 17, 2021

(30) Foreign Application Priority Data

Dec. 12, 2019 (FR) ...................................... 19 14298

(51) Int. Cl.
*A61N 5/06* (2006.01)

(52) U.S. Cl.
CPC .... *A61N 5/0622* (2013.01); *A61N 2005/0632* (2013.01); *A61N 2005/0651* (2013.01); *A61N 2005/0664* (2013.01)

(58) Field of Classification Search
CPC .......... A61N 5/0622; A61N 2005/0632; A61N 2005/0651; A61N 2005/0664; A61N 5/0601; A61N 1/0536; A61N 1/0534
See application file for complete search history.

(56) References Cited

U.S. PATENT DOCUMENTS

| | | | |
|---|---|---|---|
| 2009/0156918 A1* | 6/2009 | Davis | A61B 5/14552 600/342 |
| 2012/0165759 A1* | 6/2012 | Rogers | A61B 5/6867 606/228 |
| 2014/0228901 A1* | 8/2014 | Vogt | A61N 1/36038 607/92 |
| 2015/0306415 A1* | 10/2015 | Tischendorf | A61N 5/0601 607/92 |
| 2016/0016006 A1 | 1/2016 | Boyle | |
| 2017/0189712 A1* | 7/2017 | Lippert | A61N 5/0622 |
| 2017/0281928 A1* | 10/2017 | Orinski | A61N 1/0539 |

FOREIGN PATENT DOCUMENTS

WO   WO 2014/135197 A1   9/2014

OTHER PUBLICATIONS

French Preliminary Search Report dated Jul. 22, 2020 in French Application 19 14298 filed on Dec. 12, 2019 (with English Translation of Categories of Cited Documents & Written Opinion ), 9 pages

* cited by examiner

*Primary Examiner* — Gary Jackson
*Assistant Examiner* — Sebastian X Lukjan
(74) *Attorney, Agent, or Firm* — Oblon, McClelland, Maier & Neustadt, L.L.P.

(57) ABSTRACT

An optically stimulating module to be integrated into a probe is implantable into a living being with a view to locally illuminating a region of said living being. The module includes a casing, and a hermetic electronic unit housed in the casing. The hermetic electronic unit includes two luminous diodes connected back-to-back, and at least two electrical contacts for connecting the module to an electrical power source.

21 Claims, 10 Drawing Sheets

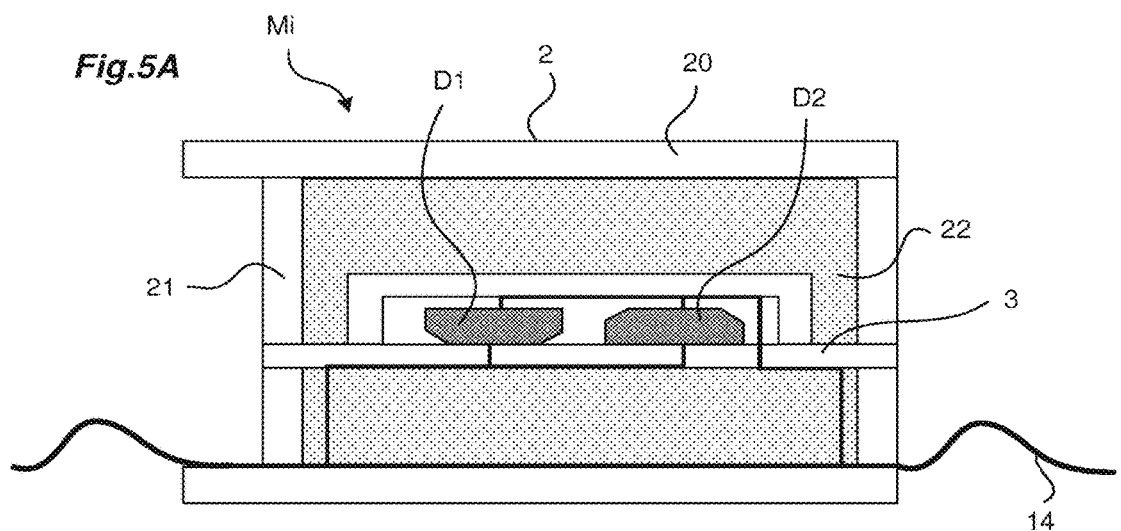
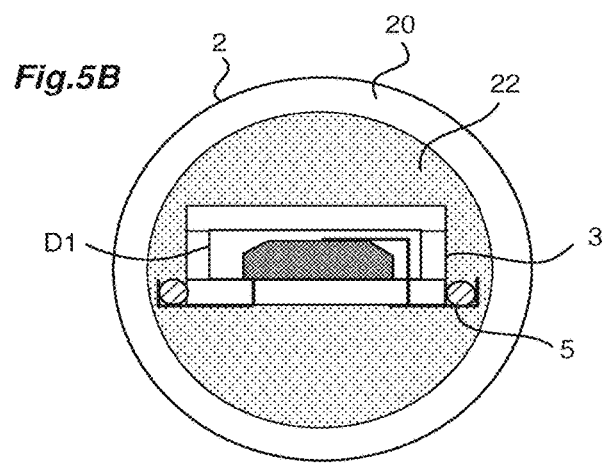
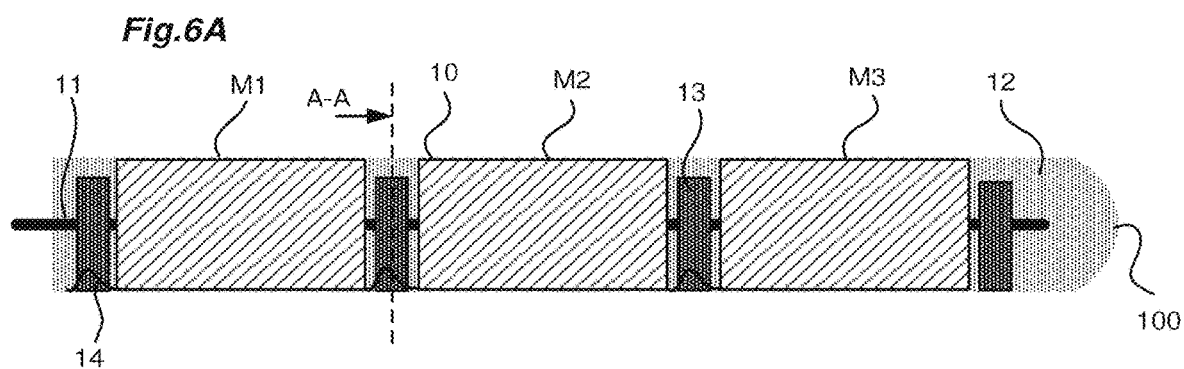
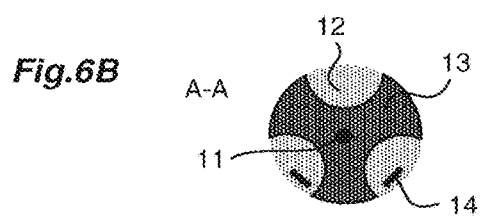

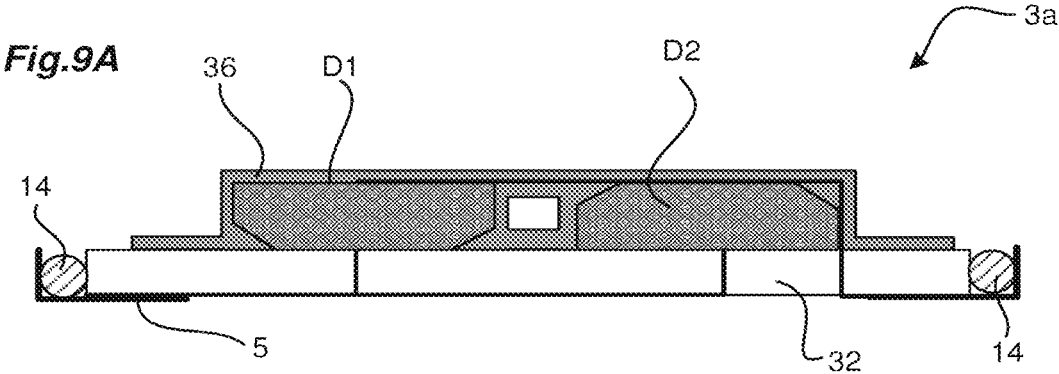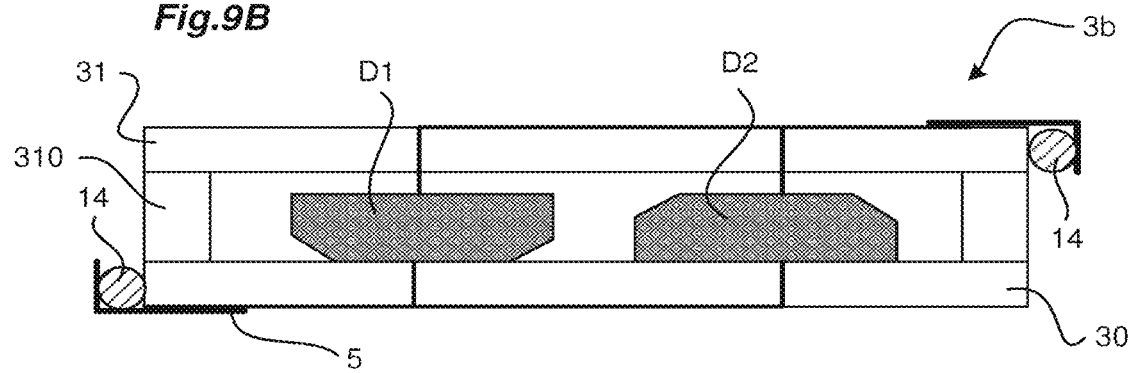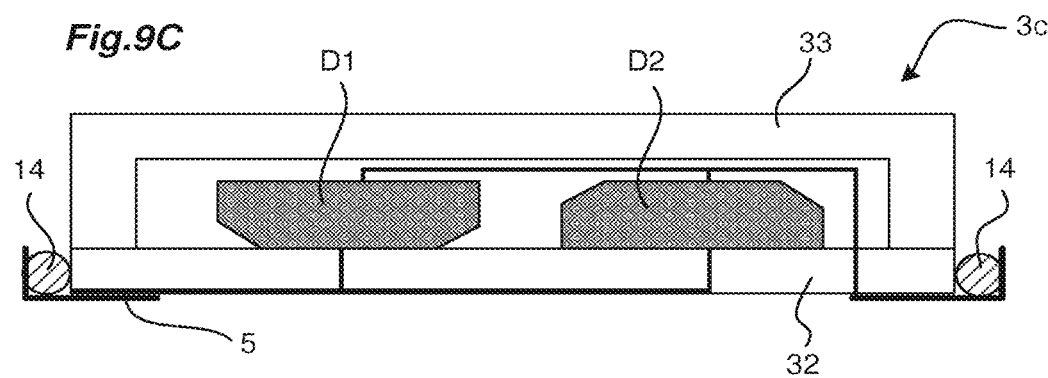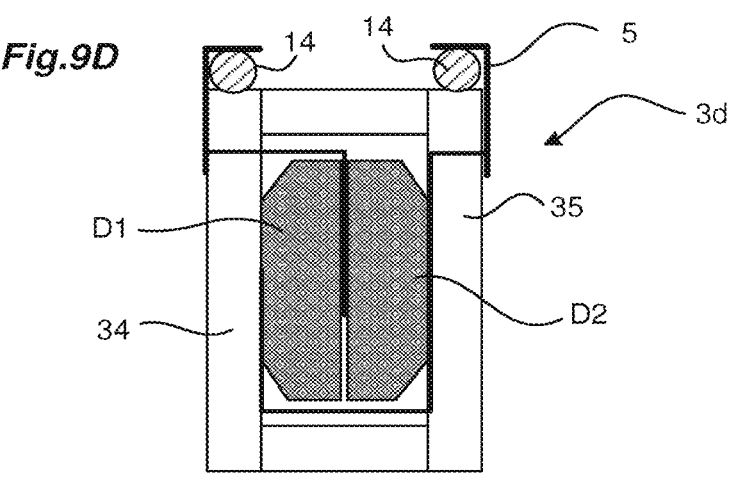

ILLUMINATING DEVICE IMPLANTABLE IN A LIVING BEING

TECHNICAL FIELD OF THE INVENTION

The present invention relates to an illuminating device intended to be at least partially implanted in a living being with a view to illuminating, locally, at least one region of the living being. The invention also relates to an optically stimulating module that allows a probe of such an illuminating device to be easily produced.

PRIOR ART

To treat certain pathologies of a living being, it has been imagined to optically stimulate an internal region of the living being. To this end, devices have been provided that comprise a light source and that are at least partially or completely implanted in the living being with a view to illuminating the desired region.

The advantageousness of optically irradiating/illuminating certain regions of the human brain with such devices has notably been observed.

However, on account of the risks related to the implantation of such a device in the brain, it will be understood that such a device must be perfectly designed.

Patent application US2017281928A1 and U.S. Pat. No. 10,213,596B2 describe implantable illuminating devices comprising an IPG (acronym of implantable pulse generator) that powers a light source, and a probe comprising a light guide tasked with delivering a light beam to the region to be treated.

These solutions do not meet the following criteria:
illumination at a wavelength tunable from 2 to 50 mm;
compatibility of a complete illumination source with IPGs available on the market (i.e. without hardware modification); and
modularity (ability to stimulate electrically and/or optically, choice of a plurality of illumination wavelengths, etc.).

The aim of the invention is to provide an optically stimulating module that is able to be easily integrated into a probe of an illuminating device, said probe being intended to be at least partially implanted into a living being, notably with a view to illuminating one or more regions of the brain thereof. The module has a suitable architecture allowing the probe to meet the various aforementioned criteria. The module may notably be easily integrated into the probe and cascaded in said probe, without modification of its architecture.

DISCLOSURE OF THE INVENTION

This aim is achieved via an optically stimulating module to be integrated into a probe that is implantable into a living being with a view to locally illuminating a region of said living being, said probe being intended to comprise a chain formed from a plurality of these modules, characterized in that it comprises:
a casing,
a hermetic electronic unit housed in said casing and comprising two luminous diodes connected back-to-back,
first electrical contacts, which are referred to as upstream electrical contacts, arranged on their casing so as to connect a first identical adjacent optically stimulating module located upstream in a chain of modules, and second electrical contacts, which are referred to as downstream electrical contacts, arranged on their casing so as to connect a second identical adjacent optically stimulating module located downstream in said chain of modules,
continuous electrical links arranged between each upstream first electrical contact and each downstream second electrical contact, and
a dedicated electrical supply contact, arranged on its casing, to which its electronic unit is connected.

According to one particularity, said electrical links comprise at least one link forming an electrical return line common to all the modules of the probe, to which link said electronic unit of the module is connected.

According to one particularity, the electronic unit comprises at least one substrate comprising two opposite faces, said two light diodes being mounted on a single one of the two faces of said substrate.

According to another particularity, the electronic unit may comprise a suitable hermetic cover on the substrate.

According to another particularity, the electronic unit may comprise a deposit produced by ALD covering the two luminous diodes.

According to another particularity, the electronic unit may comprise two substrates, on each of which one separate luminous diode is mounted.

According to another particularity, the casing of the module may comprise a ring that is closed at its to ends by two plugs, said two plugs bearing means for holding the electronic unit housed in the casing.

According to another particularity, the module may comprise stimulating electrodes on the lateral surface of its ring.

According to another particularity, the module may comprise a coating material injected into its casing around the hermetic electronic unit.

The invention also relates to a probe that is implantable into a living being, said probe being intended to be electrically connected to an electrical power source and having an elongate architecture, characterized in that it comprises a plurality of optically stimulating modules juxtaposed along the probe and separated from each other by a non-zero distance, said probe comprising a coating material that fills the space between two adjacent modules, each optically stimulating module being such as defined above, said probe comprising a plurality of electrical paths each intended to be electrically connected, point-to-point, to one separate electrical path of the electrical power source, each optically stimulating module of the probe being connected in series on a separate electrical path of the probe via its dedicated electrical supply contact.

According to one particularity, the probe comprises a reinforcement formed of a wire over which said modules are slipped.

According to another particularity, between two adjacent modules, the probe comprises a mechanically dividing ring slipped over said reinforcement.

According to another particularity, the probe comprises an axially illuminating module located in proximity to the distal end of the probe.

The invention also relates to an implantable illuminating device intended to be implanted into a living being with a view to locally illuminating a region of said living being, said device comprising an electrical power source comprising a plurality of parallel electrical supply paths and a probe that is electrically connected to the electrical power source and that has an elongate architecture between a proximal end and a distal end, said probe being such as defined above.

According to one particularity, the electrical power source is an implantable pulse generator.

BRIEF DESCRIPTION OF THE FIGURES

Other features and advantages will become apparent from the following detailed description, which is given with reference to the appended drawings listed below:

FIGS. 5A and 5B show, seen from the side and axially, respectively, a module employed in the device of the invention, according to the first example of an embodiment of FIGS. 4A and 4B;

FIGS. 6A and 6B show a second example of an embodiment of the probe according to the invention, via a schematic view from the side and via a view in cross section along A-A, respectively;

FIGS. 9A to 9D show four embodiments of the holder of the luminous diodes that is employed in the device of the invention;

FIG. 11A is a view from the side in longitudinal cross section; FIGS. 11B, 11C and 11D are views in cross section and FIG. 11E is a view from above;

DETAILED DESCRIPTION OF AT LEAST ONE EMBODIMENT

The invention relates to an implantable illuminating DBS device 1 (DBS being the acronym of deep brain stimulation). This device notably allows localized illumination (for example in the near infrared or with any other wavelength depending on the envisioned treatment—neuroprotective treatment, optogenetic treatment, etc.) of target tissues (for example the SNc, hippocampus, striatum, etc.) to be carried out while minimizing the medical risks of the implantation. This device may in particular be used to treat neurodegenerative diseases such as Parkinson's disease, Alzheimer's disease, Huntington's disease, etc.

Figure 13A:
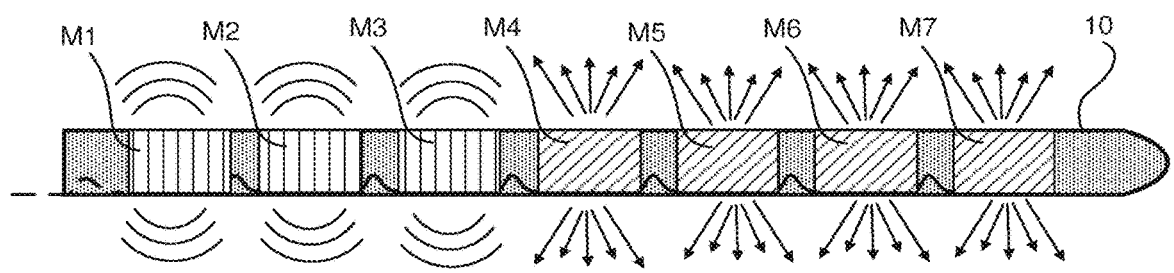
FIGS. 13A to 13C show three examples of an embodiment of a hybrid probe able to be employed in the device of the invention.
Figure 13B:
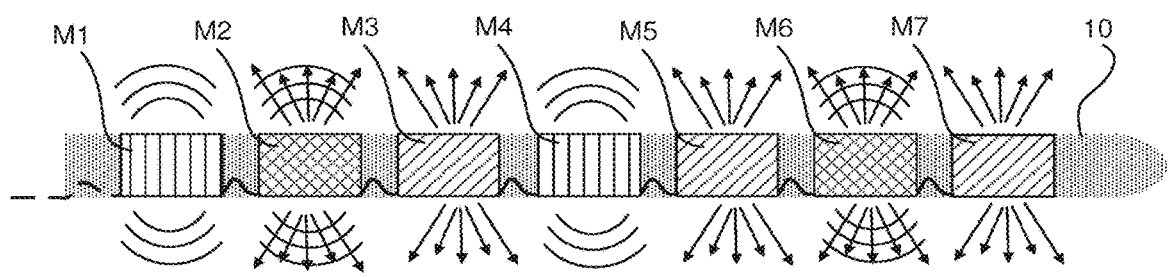
Figure 13C:
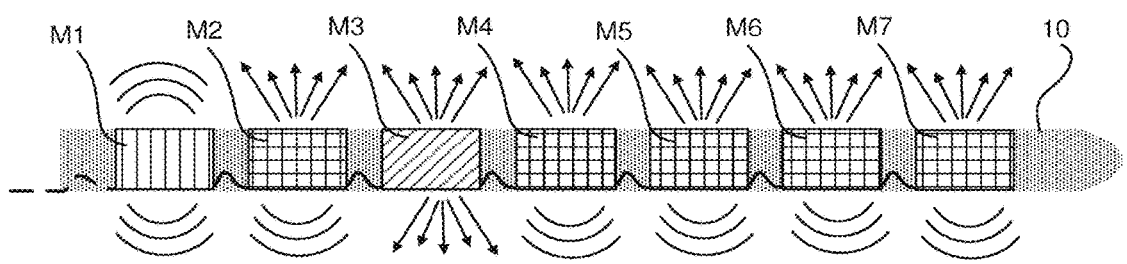

It will be seen that the device 1 may optionally incorporate solutions enabling other modes of stimulation (electrical, injection, etc.). FIGS. 13A to 13C illustrate the principle of hybrid stimulation.

The illumination of the tissues may have various objectives depending on the application: neuroprotection, optogenetics, stimulation, etc. A number of targets are concerned, for example: the substantia nigra pars compacta (SNc), which degenerates in Parkinson's disease; the hippocampus, main center implicated in Alzheimer's disease; and the striatum for Huntington's disease. The illumination may be delivered directly to the tissues (with risk of additional lesions) or via routes passing through the ventricles (cavities allowing cerebrospinal fluid (CSF) to circulate) and making contact with the structures to be treated (directional illuminator).

The device 1 of the invention comprises an electrical power source. This power source is advantageously composed of an implantable pulse generator (commonly called an IPG), referenced IPG in the drawings.

Figure 3A:
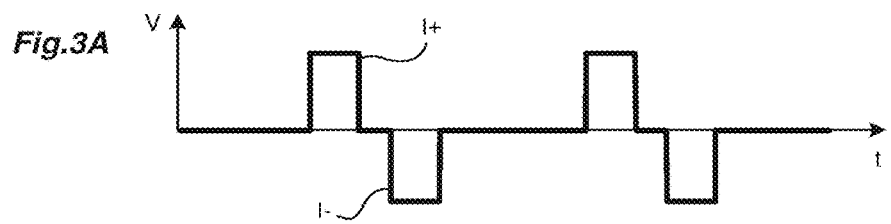
FIGS. 3A and 3B illustrate various types of voltage signals able to be emitted by the generator employed in the device of the invention.
Figure 3B:
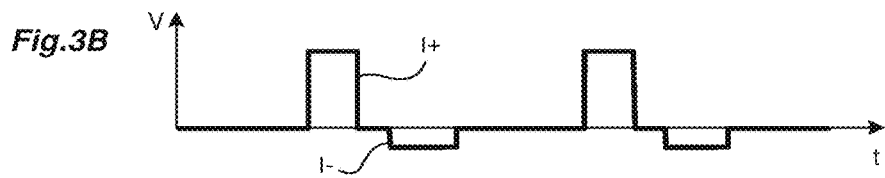

As known, an IPG mainly comprises a circuit board and a battery, which may or may not be rechargeable. The circuit board comprises a microcontroller that is responsible for managing the operation of the generator. The IPG may notably be programmed to deliver what are referred to as bipolar pulses, such as those shown in FIGS. 3A and 3B. In FIGS. 3A and 3B, the waveform thus comprises a positive square pulse I+ and a negative square pulse I−, which are separated from each other by a dead time. To balance the electrical charges injected into the tissues, the two pulses may be symmetric (as illustrated in FIG. 3A) or modulated in amplitude and in duration (as illustrated in FIG. 3B), with the same amount of charge injected during both pulses (t×current×voltage with t the duration of the pulse). The generator comprises n paths, with n higher than or equal to 2. Each path is referenced Vi with i ranging from 1 to n.

The device 1 then comprises an implantable probe 10 connected to the generator.

This implantable probe 10 takes the form of a supple elongate stem. The probe 10 advantageously has a circular cross section. By way of example, the diameter of the cross section of the probe may range from 1 to 3 mm, and is preferably 1.3 mm in order to be compatible with the standard tools used in DBS.

The device 1 comprises electrically connecting means allowing the probe 10 to be connected to the IPG via its proximal end, by way of a connector 15 and an extension 16. At the distal end, the probe 10 advantageously has an atraumatic shape 100 (for example an oblong or spherical shape).

According to the invention, over at least some of its length, the probe 10 incorporates a plurality of juxtaposed optically stimulating modules forming a strip. This strip is advantageously located in proximity to the distal end of the probe 10.

The number of modules of the probe may be tailored to the pathology to be treated and to the size of the region of tissue treated (which may for example range from 5 to 50 mm in length).

Figure 1:
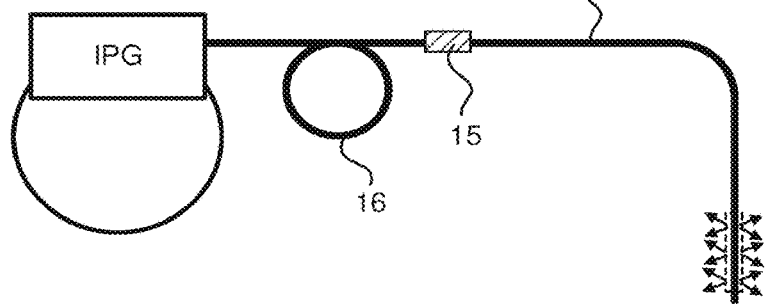
FIG. 1 shows an example of an embodiment of the device according to the invention.
Figure 2A:
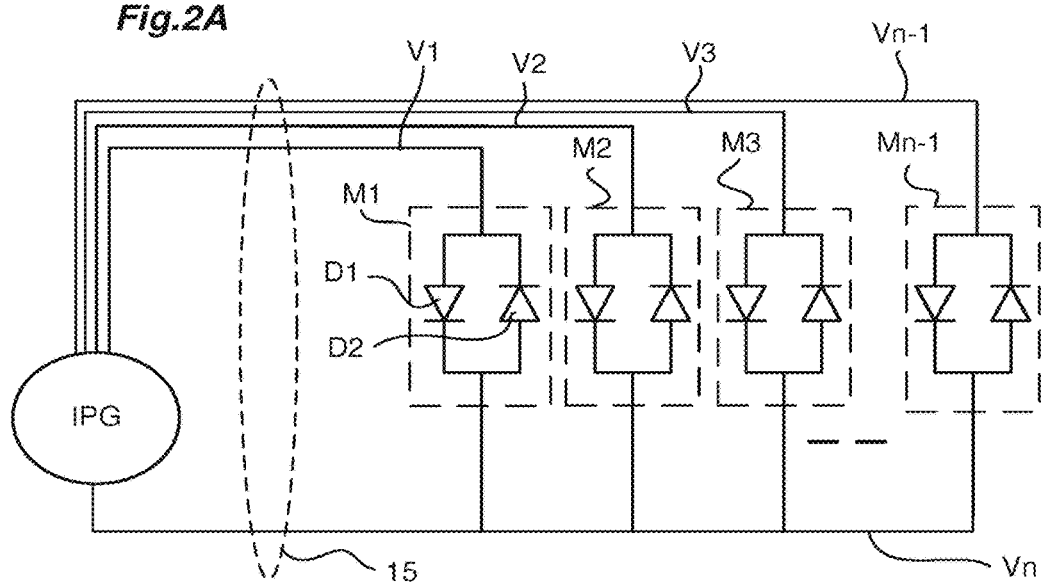
FIGS. 2A and 2B show the electrical architecture of the device of the invention, according to two exemplary embodiments.
Figure 2B:
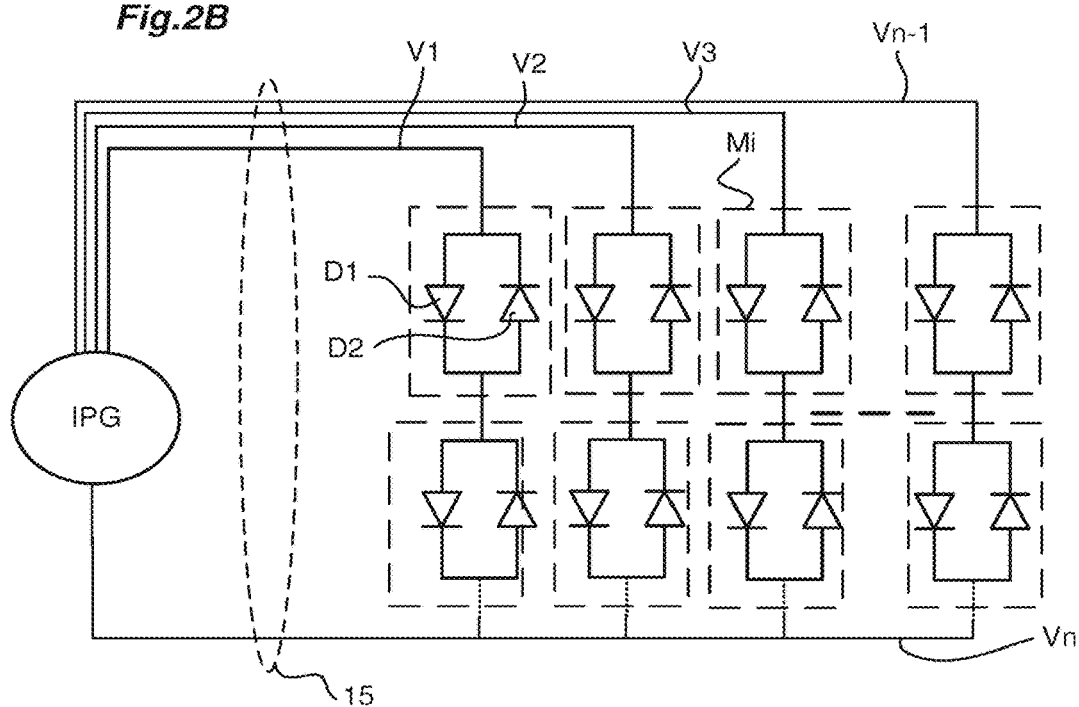

In FIGS. 2A and 2B, the optically stimulating modules are referenced Mi, with i ranging from 1 to n−1 with n higher than or equal to 3 (n corresponding to the number of paths of the employed IPG). The probe thus comprises at least two optically stimulating modules that are connected in parallel to the IPG. By way of example, the generator may comprise 8 or 12 paths.

In the device, the modules are connected point-to-point to the IPG and may thus be individually addressed thereby. Each module or series of modules (at least two modules wired in series on each path as in FIG. 2B) is thus connected on one separate path Vi of the generator. A single return link allows all of the modules to be connected on one path of the IPG. A scheme of connection of each module in the chain will be described below with reference to FIG. 8A.

Figure 4A:
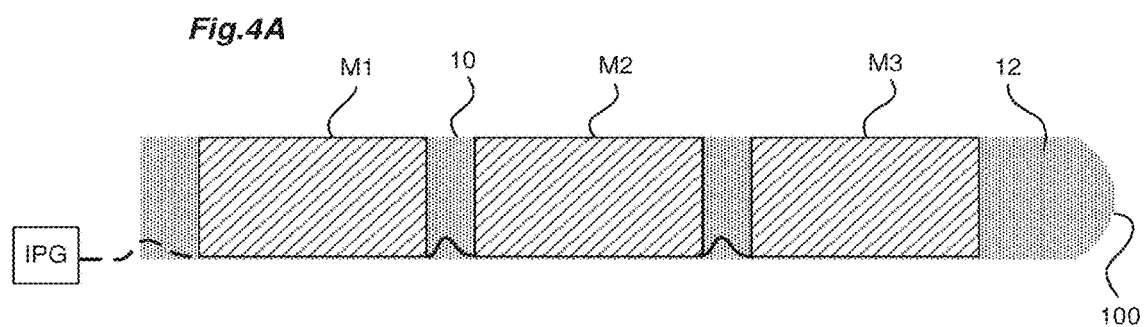
FIGS. 4A and 4B show a first example of an embodiment of the probe according to the invention.
Figure 4B:
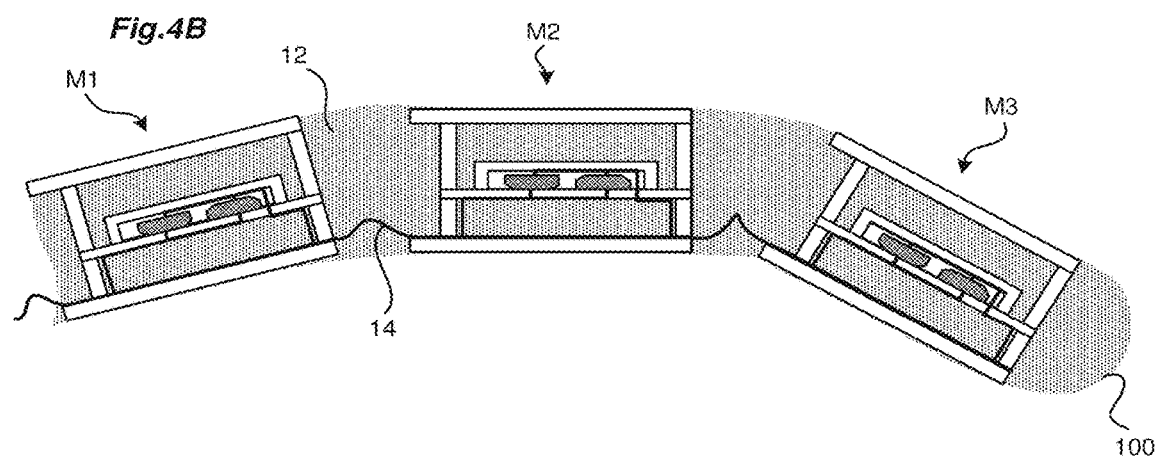

With reference to FIGS. 4A and 4B, in a first example of an embodiment, the modules Mi are connected to one another so as to form a daisy chain and are held together by a coating material 12 such as silicone, polyurethane or epoxy, the material possibly being chosen notably depending on the rigidity required for the application. Each module Mi is connected to the IPG by a point-to-point link. A first clad and insulated electrical conductor 14 allows all of the paths of the IPG to be routed to the modules. A second electrical conductor, which is also clad and insulated, may form the electrical return link to the IPG. Any other electrical wiring solution may be employed.

With reference to FIGS. 6A and 6B, in another example of an embodiment, the probe 10 may comprise a reinforcement 11, for example formed from a central (rigid or supple as required) core such as a metal wire securely fastened to the modules, the silicone, polyurethane or epoxy coating 12 filling the space between modules. The polyurethane coating notably allows the probe to be preformed as required. The wire forming the reinforcement 11 allows the elongation of the probe 10 during the manipulation of the device, and notably during its surgical insertion and the various cleaning steps during production, to be limited. The modules Mi are separated from one another along the reinforcement 11 by a non-zero length, by the coating material 12, so as to keep regions of flexion and to allow the probe 10 to preserve a certain level of flexibility. The wire 11 may moreover serve as a "ground plane" for the return of current from all of the supply tracks.

The modules are slipped onto the reinforcement 11, the latter being placed directly in line with the modules Mi. A dividing ring 13 that is slipped onto the reinforcement 11 may be positioned between two adjacent modules Mi, in order to limit the flexion applicable to the probe to a set range, notably with a view to protecting the electrical connection and to facilitating surgical placement of the implant. As shown in FIG. 6B, each dividing ring 13 may have the shape of a star with a plurality of vertices, this allowing the coating material to flow between two modules in order to form the joint and a space to be left for the passage of the conductors 14 from one module to the next.

With reference to FIGS. 5A, 5B, 7A and 7B, each optically stimulating module Mi may comprise a casing 2. The casing 2 may comprise a ring 20 made of a transparent and biocompatible material such as sapphire or silica and closed at its two ends by plugs 21, so as to form a hollow cylinder. The cylinder may have an outside diameter of 1300 µm.

Figure 7A:
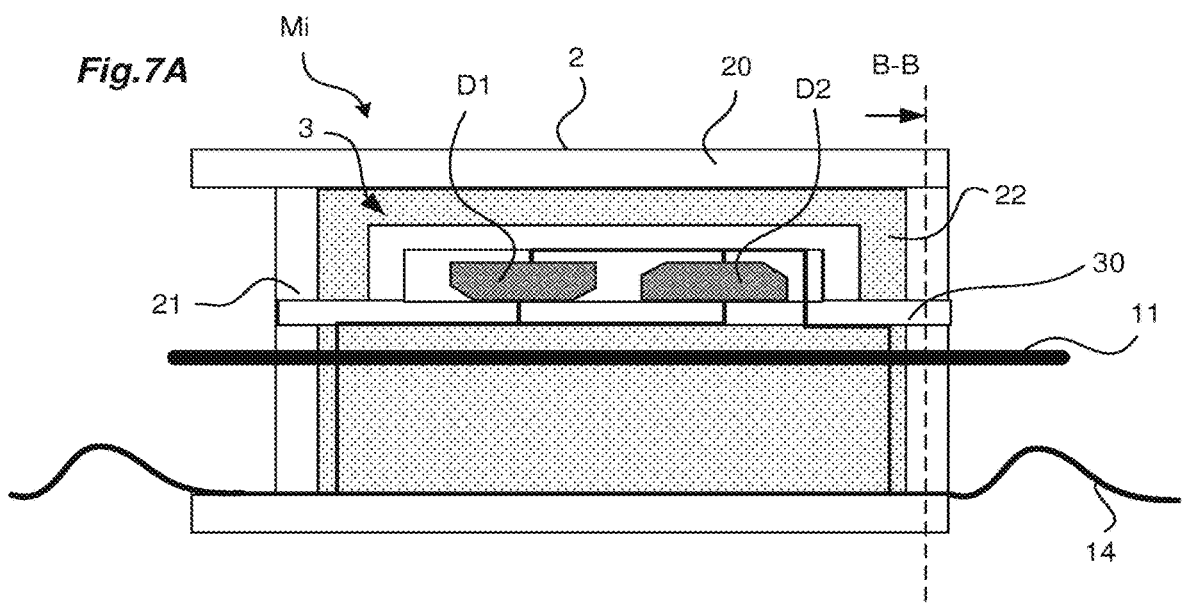
FIGS. 7A and 7B show, seen from the side and in cross section along B-B, respectively, the module employed in the device of the invention, according to the second example of an embodiment of FIGS. 6A and 6B.
Figure 7B:
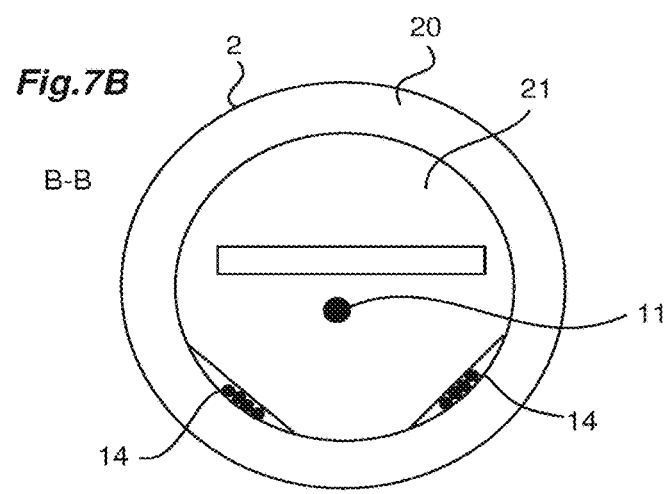

The module Mi comprises a hermetic electronic unit 3 housed in its casing. The two plugs 21 are used to correctly position the electronic unit and to facilitate filling of the cavity with a coating material 22, which may be a transparent or scattering material depending on the sought-after uniformity objective (silicone, polyurethane or epoxy). An epoxy adhesive with a refractive index limiting losses by reflection will possibly be selected, and will possibly also be combined with a filler in order to improve heat transfer and seal-tightness, and to meet constraints on expansion during production (in particular for chips passivated by ALD—see below). As shown in FIGS. 7A and 7B, the two plugs 21 may be drilled in their center to let the reinforcement 11 of the probe 10 pass. In the probe, each module Mi is thus independent of each other module and has its own electronic architecture, i.e. its electronic unit (see the description given below in connection with FIGS. 9A to 9D) and its connecting electrical contacts, and its own mechanical architecture, the latter being composed of the ring and plugs. It should be noted that each module of the electronic unit is hermetic, making each module easy to integrate into a probe during its manufacture.

Each module Mi comprises a light source housed in its electronic unit. The light source may comprise at least two luminous diodes produced in known technologies (LEDs, OLEDs, µLEDs, VCSELs, lasers, etc.). The diodes may operate at a voltage lower than a few volts (2 V for example for LEDs), with currents possibly ranging from 2 to 25 mA. The IPG may, for its part, deliver a voltage of 15 V and currents ranging from 25 to 50 mA, this for example allowing a plurality of components in series (for example up to seven diodes of 2 V) to be powered. In the case of VCSEL diodes (VCSEL being the acronym of vertical-cavity surface-emitting laser) or laser diodes, the duration and amplitude of the pulses delivered by the generator may be tailored. The area generated by two pulses will necessarily be chosen to be identical, i.e. the same amount of charge will be injected by each of two pulses.

All the modules Mi of the probe are identical, notably as regards their electrically connecting means. To connect each thereof to one separate path Vi of the IPG and on the return path Vn of the IPG, while ensuring an electrical continuity over the entire length of the chain of modules present in the probe, each module Mi comprises various electrically connecting means.

Figure 8A:
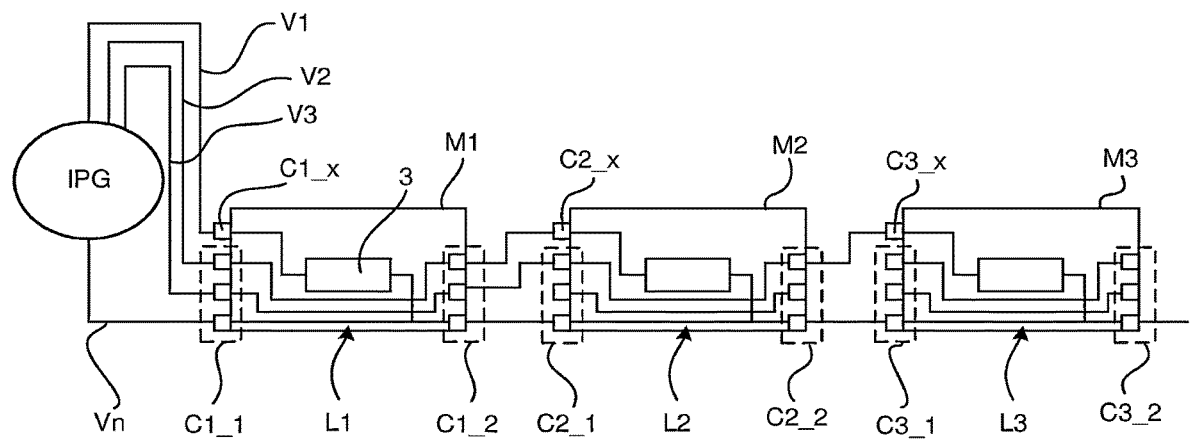
FIG. 8A shows a preferred embodiment of the probe of the device of the invention.

With reference to FIG. 8A, each module Mi (M1, M2, M3 in FIG. 8A) thus comprises first electrical contacts $Ci\_1$, which are referred to as upstream electrical contacts, arranged on their casing 2 to connect the module Mi−1 located downstream in the chain of modules, and second electrical contacts $Ci\_2$, referred to as downstream electrical contacts, arranged on their casing 2 to connect the module Mi+1 located downstream in said chain of modules. Continuous (uninterrupted) electrical links Li are arranged to link each upstream first electrical contact to each downstream second electrical contact and thus to ensure an electrical continuity from one module to another.

Moreover, the electrically connecting means of the module Mi comprise, arranged on its casing, a dedicated electrical supply contact $Ci\_x$ connected on the one hand point-to-point to a single path Vi of the IPG and on the other hand to the electronic unit 3 of the module Mi with a view to supplying power thereto. Among said aforementioned electrical links, one thereof forms the return link Vn to which the electronic unit 3 of the module Mi is connected. It should be noted that the number of links Li of the module defines the number of modules (or groups of a plurality of modules in series) that the chain is capable of incorporating. This number of modules will be at most equal to the number of paths available in the IPG. If the IPG comprises 12 paths, each module comprises one electrical contact dedicated to the supply of power to its electronic unit 3, and 11 electrical links Li. After the first module M1 of the chain, each module has its dedicated electrical contact $Ci\_x$ connected to a separate point-to-point link.

The module M1 of rank 1 in the chain is located at the proximal end of the probe and connected on the upstream side to all the paths of the IPG.

Specific electrical contacts may be provided on each module if the module also comprises electrically stimulating means.

Figure 8B:
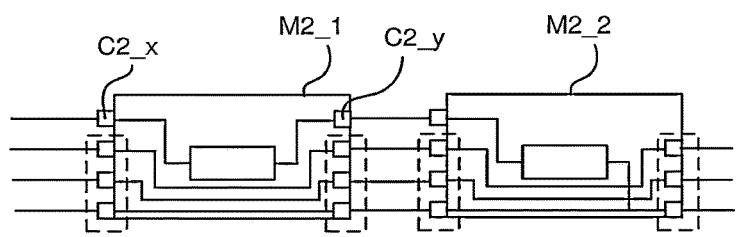
FIG. 8B illustrates a variant embodiment of the architecture of FIG. 8A.

In the case where two modules are connected in series on the same path (as in FIG. 2B), the first module of the series may have an architecture tailored thereto. FIG. 8B illustrates this particular embodiment, for two modules M2_1, M2_2 connected in series on the same path of the generator. The first module M2_1 of the series comprises a dedicated downstream electrical contact, referenced C2_y, its electronic unit 3 then being directly connected between its upstream electrical contact C2_x and its downstream electrical contact C2_y. The second module M2_2 of the series is identical to the module Mi described above in connection with FIG. 8A. The upstream and downstream electrical contacts, and the electrical links described above, in connection with FIG. 8A are reproduced identically in the two modules M2_1 and M2_2 connected in series.

Advantageously, the light source of each module Mi is composed of at least two luminous diodes D1, D2 connected back-to-back. One of the two diodes is thus active during the positive-voltage pulse I+ delivered by the IPG and the other is active during the negative-voltage pulse I− delivered by the generator. This arrangement thus allows all the available power to be used, while protecting the luminous diodes from reverse bias.

In each module Mi, the two luminous diodes D1, D2 may be identical and emit the same wavelength. However, it is also possible to make provision to use two diodes that emit at two separate wavelengths, for example 670 nm for one and 810 nm for the other. If it is desired to illuminate at two wavelengths, it will be useful to employ VCSEL diodes or any other type of laser diodes instead of LEDs, in order to tune the power at the two wavelengths independently, by adjusting the width/amplitude of the positive and negative pulses delivered by the IPG.

The illumination is carried out in a plurality of directions that are transverse (and notably radial in a probe of circular cross section) to the axis of the probe. Depending on the modules employed, it will be seen that it is possible to illuminate in various directions, over the entire periphery of the probe or in a narrower defined angular range (see FIGS. 10A to 10D). It will notably be possible to employ bidirectional illuminating modules (for example 2×110°) or more directional illuminating modules (for example 1×110°).

The two luminous diodes D1, D2 are assembled (via conductive adhesive or welding) and integrated into said hermetic electronic unit 3. They are therefore protected inside the electronic unit.

Nonlimitingly, the diodes may be mounted in the electronic unit 3 according to a plurality of possible variants. The luminous diodes D1, D2 may thus be mounted on one or both faces of a substrate of the electronic unit 3 or on the two separate faces of the substrate of the electronic unit, depending on the desired type of illumination (for example illumination over an angle of 110° or 2×110°).

In FIG. 9A, the electronic unit 3a comprises a single, opaque or transparent, substrate 32 that incorporates "vias" to transmit electrical signals, on which substrate the two luminous diodes D1, D2 are juxtaposed and interconnected. A conformal deposit 36 is produced by ALD (atomic layer deposition) on all of the face holding the diodes, in order to encapsulate them and isolate them from the exterior, allowing the electronic units to be made hermetic.

In FIG. 9B, the electronic unit 3b comprises two (silica or sapphire) opaque or transparent substrates 30, 31 comprising vias and metal tracks for supplying the luminous diodes with power. The two substrates 30, 31 are joined together, by virtue of a spacer 310, for example by laser welding or soldering and form a hermetic assembly in which the two luminous diodes D1, D2 are housed. The two luminous diodes D1, D2 are fastened (for example via conductive adhesive or soldering) to the top face of the first substrate 30. In the embodiment of FIG. 9B, electrical tracks and vias of the circuit are produced on/in both substrates 30, 31.

In FIG. 9C, the electronic unit 3c comprises a single electronic substrate 32 and a cover 33. The two luminous diodes are adhesively bonded or soldered to the electronic substrate 32 and the cover 33, which may be transparent, is hermetically attached to the substrate to enclose said diodes. In the embodiment of FIG. 9C, electrical tracks and vias of the circuit are produced only on/in the substrate 32.

The two luminous diodes D1, D2 may be juxtaposed in the same plane, as in FIGS. 9A, 9B and 9C, or juxtaposed in a superposed manner as in FIG. 9D.

In the embodiment of FIG. 9D, the electronic unit 3d also comprises two electronic substrates 34, 35 that are joined together to form a hermetic assembly in which the two luminous diodes D1, D2 are housed. The first diode D1 may be fastened to the top face of the first substrate 34 and the second diode D2 may be fastened to the bottom face of the second substrate 35 and positioned just above the first diode.

In the four configurations, each substrate may, for example, have a length of 1000 μm, while each diode D1, D2 may extend over a length smaller than or equal to 350 μm over a substrate.

As indicated above with reference to FIG. 8A, the electronic unit 3 of the module Mi is connected to a path Vi of the generator and to the return path Vn, via the electrically connecting means of the module. The electronic unit 3 may comprise electrical contacts 5 that are arranged on either side of each unit 3 and that each clasp one separate conductor 14, a first conductor being connected to the dedicated electrical supply contact Ci_x of the module with a view to connection to its supply path Vi, and a second conductor connecting to the electrical link of the module that corresponds to the return path Vn leading to the IPG.

In the four configurations, conventional microelectronic techniques are employed to produce the electrical tracks, solder the light-emitting diodes and to produce the required electrical connections. It will possibly be a question of welding, soldering, adhesive bonding and screen-printing techniques etc. The diodes will be assembled on each substrate and the hermetic assembly will be produced using known techniques such as laser welding and multilayer ALD (ALD being the acronym of atomic layer deposition).

In each module, the one or more substrates are oriented in a direction parallel to the axis of the module (and therefore to the axis of the probe 10 when the modules are assembled with one another). In this configuration, the luminous diodes D1, D2 are oriented to illuminate, with respect to the axis of the probe 10, transverse directions. In each module Mi, the illumination may occur via all the lateral surface of the probe or be limited to a given lateral angular range. A mask may for example be produced on the lateral surface of the probe, with a view to orienting the illumination in one or more given lateral directions.

Depending on the configuration, nonlimitingly, each substrate 32 may be opaque or at least partially transparent in order to let the light emitted by the luminous diodes pass without inappropriate masking. The layout of the masking due to the conductive tracks and the extent of the transparency of the ring will possibly be tailored to the orientation of the luminous diodes and to the degree of scattering of the light. Each module may thus be configured to create a directional or isotropic illumination.

Figure 10A:
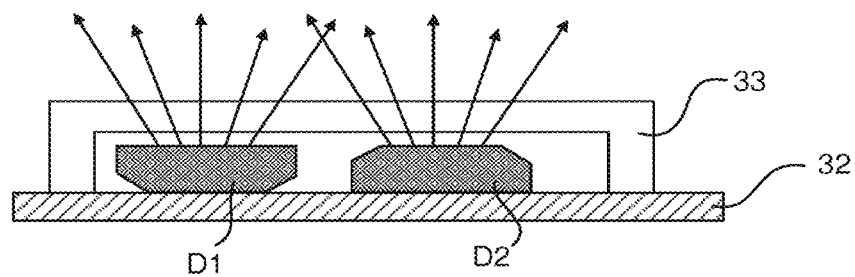
FIGS. 10A to 10D illustrate various illuminating configurations permitted by the device of the invention.
Figure 10B:
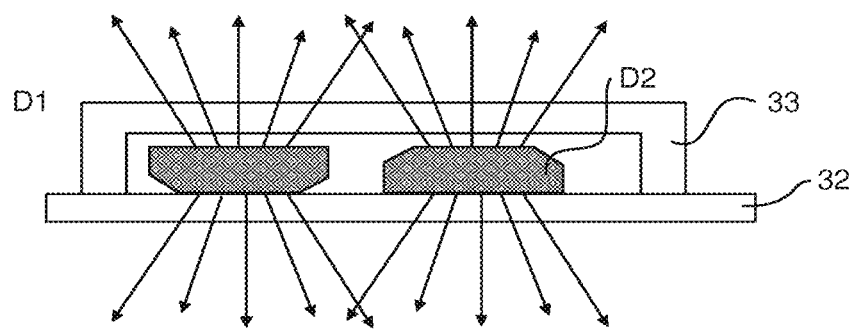
Figure 10C:
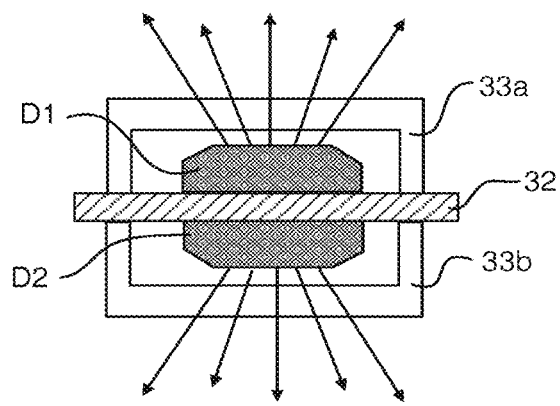
Figure 10D:
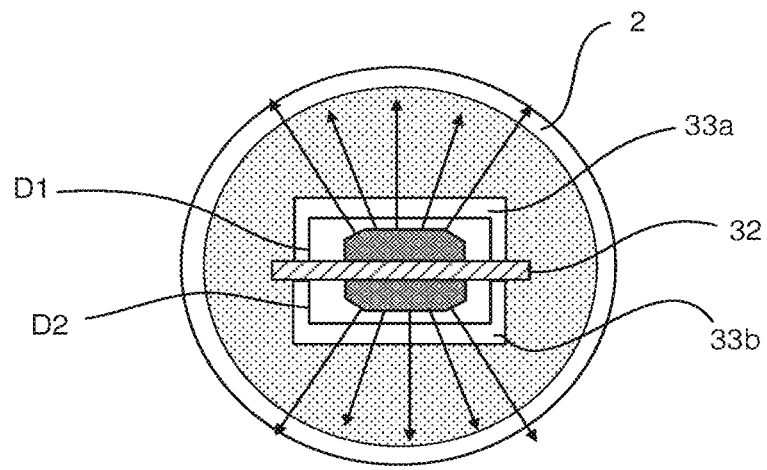

FIGS. 10A to 10D illustrate various possible illumination configurations. In FIG. 10A, the module comprises two diodes fastened to the same face of an opaque substrate 32. The cover 33 is chosen to be transparent. The illumination is thus produced only on a single side. In FIG. 10B, the substrate 32 is transparent and the cover 33 is transparent, allowing light to be emitted from both sides. In FIG. 10C, the module comprises two diodes D1 and D2 that are fastened to the two opposite faces of the same opaque substrate, allowing emission on both sides through two transparent covers 33a, 33b. In FIG. 10D, it may be seen that the configuration of FIG. 10C allows emission around the entire periphery of the probe.

The holder of the luminous diodes D1, D2 is housed in the casing 2 of each module Mi and is then coated by a coating material such as silicone, polyurethane or epoxy.

As illustrated in FIG. 2, the IPG is configured to present a plurality of paths Vi, with i ranging from 1 to n. As one path (Vn) of the generator is reserved for the return signal, the generator has n−1 paths available for the connection of the modules. It should be noted that it is possible to connect at least two modules in series on the same path, as on the path Vn−1 shown in FIG. 2. By way of example and nonlimitingly, the generator may comprise 8 to 12 paths per channel and up to 4 independent channels.

Figure 11A:
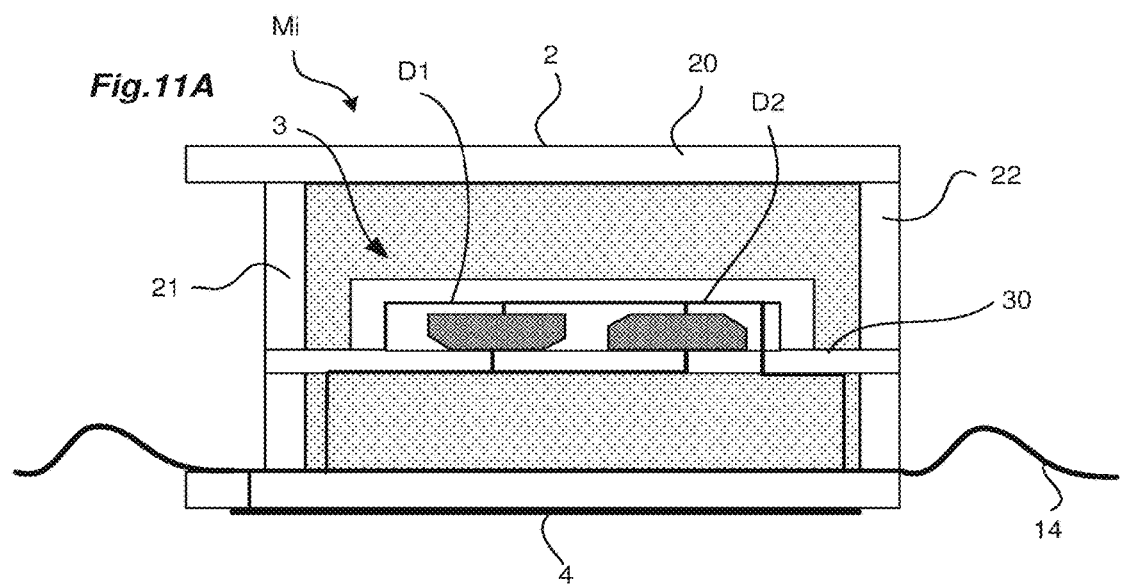
FIGS. 11A to 11E show examples of an embodiment of the electrodes present on the surface of the module.
Figure 11B:
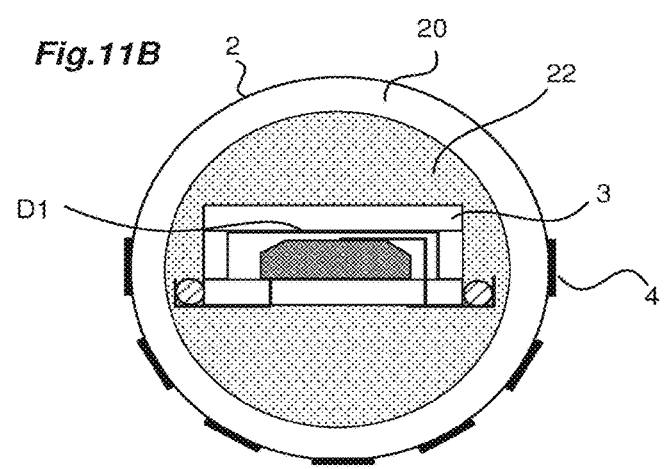
Figure 11C:
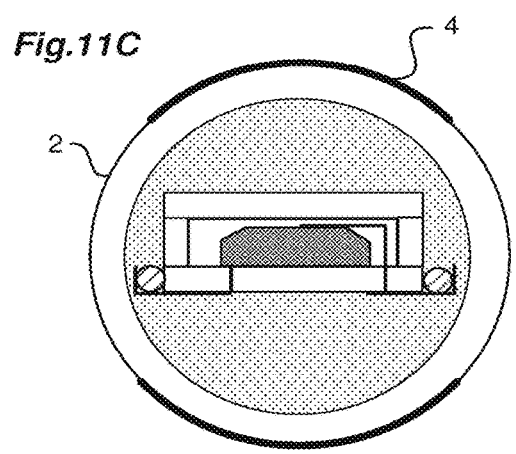
Figure 11D:
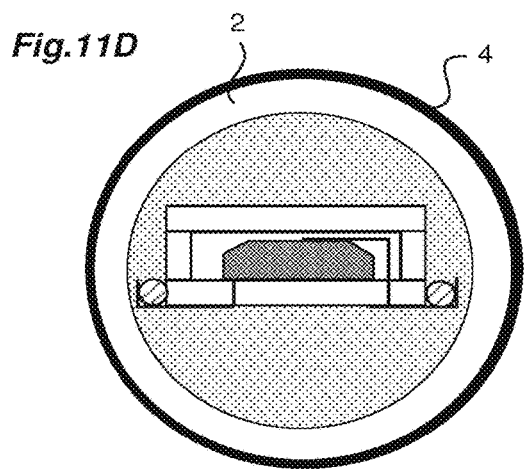
Figure 11E:
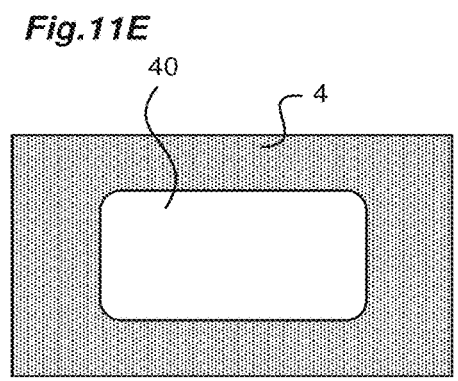

The module of the invention may also be of hybrid type, i.e. comprising optically stimulating means and electrically stimulating means. In this case, as shown in FIGS. 11A and 11B, the module Mi, in addition to bearing the luminous diodes D1, D2, also bears electrodes 4 allowing surrounding tissues to be stimulated electrically. These electrical contacts 4 may be arranged on at least one portion of the surface of the side wall of the cylindrical casing 2 of the module Mi. The electrodes 4 may be connected to the same IPG as that employed to power the luminous diodes and occupy certain paths of the paths of the generator. The electrodes, which are deposited locally in order to let the optical beam pass, may be made of bulk or sputtered platinum-iridium or of IrO2. In FIG. 11B, the electrodes 4 are flat strips that extend in a direction parallel to the axis of the ring of the module. In FIG. 11C, the electrodes 4 are circularly arcuate and extend over an angular segment of the ring. In FIG. 11D, the electrode 4 is ring-shaped and extends over the entire lateral surface of the ring. In FIG. 11E, the electrode is produced in the form of a localized deposit, allowing an aperture 40 to be left for the optical beam.

When a module is hybrid, i.e. when it possesses both optically stimulating means and electrically stimulating means, it should be noted that it may operate in either of the two stimulating modes or in both stimulating modes simultaneously.

Figure 12:
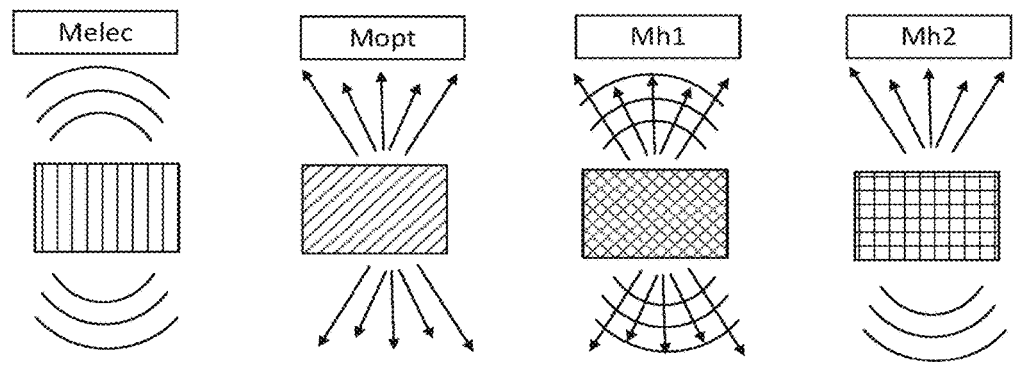
FIG. 12 schematically illustrates the various types of modules able to be employed in the probe of the invention.

With reference to FIG. 12, in the same probe 10, it is possible to use various types of module, i.e.:
one or more optical modules Mopt only able to stimulate optically;
one or more electrical modules Melec only able to stimulate electrically; and
one or more hybrid stimulating modules Mh1, Mh2 able to stimulate electrically and/or optically.

Hybrid stimulating modules may operate in various ways. It is notably possible to use a partial optical stimulation and a partial electrical stimulation (module Mh2 in FIG. 12) or to activate all the stimulating means thereof simultaneously (module Mh1 in FIG. 12).

Of course, the hybrid stimulating module may operate in optical and/or electrical mode and is thus more adaptable.

FIGS. 13A, 13B and 13C illustrate three examples of an embodiment of a hybrid probe able to employ these various types of module. These examples must be considered to be nonlimiting, and it will be possible to provide any other combination of modules.

In FIG. 13A:
modules (M1, M2 and M3) are made to generate only electrical stimulation, to perform an STN stimulation for example; and
modules (M4, M5, M6 and M7) are made to generate only optical stimulation, to perform an SNc stimulation.

In FIG. 13B:
modules (M1 and M4) are made to generate only electrical stimulation;
modules (M3, M5 and M7) are made to generate only optical stimulation; and
modules (M2 and M6) are made to generate hybrid (optical and electrical) stimulation.

In FIG. 13C:
modules (M2, M4, M5, M6 and M7) are made to generate optical stimulation in a first angular range of the probe and electrical stimulation in a second angular range.

Figure 14:
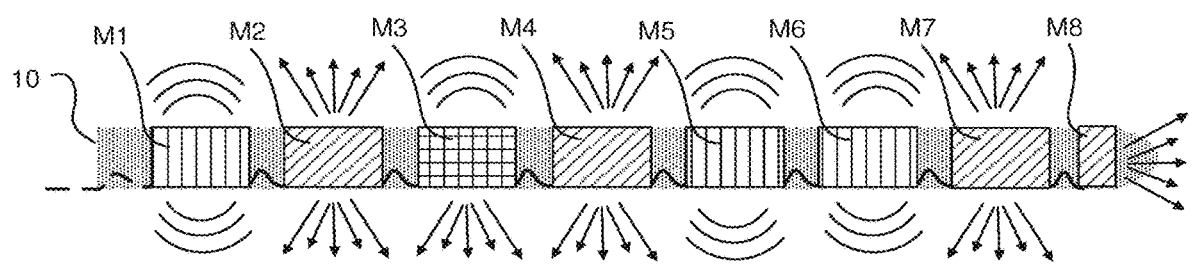
FIG. 14 shows another embodiment of the probe of the invention.

FIG. 14 shows another embodiment of the probe 10 of the invention. In this embodiment, an axially illuminating module M8 is integrated into the distal end of the probe 10. This module may have similar characteristics to those of the laterally illuminating modules described above. The holder of these diodes may be oriented transversely with respect to the axis of the probe 10.

It should be noted that the use of a pulse generator and the back-to-back layout of the luminous diodes in each module allows the risks to the patient in case of current leakage to be limited, leakage currents needing to be limited to 1 μA on average. These levels of leakage current are difficult to achieve when the electric power supply is a DC or monopolar supply.

Moreover, use of identical and independent modules to be connected to one another allows a probe to be easily put together. A manufacturer will moreover easily be able to adapt the probe to his needs by selecting the right number of modules and by selecting the modules to be used, depending on the wavelength to be emitted, on the number of wavelengths to be emitted per module, on the type of illumination to be obtained, and on the desired (optical and/or electrical) stimulation.

The invention claimed is:

1. An optically stimulating module to be integrated into a probe that is implantable into a living being with a view to locally illuminate a region of said living being, said probe being configured to comprise a chain formed from a plurality of these modules, wherein the module comprises:
 a casing,
 a hermetic electronic unit housed in said casing and comprising two luminous diodes connected back-to-back,
 at least one substrate mounted in the casing, and
 upstream electrical contacts, arranged on the casing and configured to connect to a first identical adjacent optically stimulating module located upstream in the chain of modules, and downstream electrical contacts, arranged on the casing and configured to connect to a second identical adjacent optically stimulating module located downstream in the chain,
 electrical links arranged between each upstream electrical contact and each downstream electrical contact, and a first dedicated electrical supply contact, arranged on its casing, to which its electronic unit is connected, wherein the casing is configured to enclose the hermetic electronic unit independently from another module.

2. The module as claimed in claim 1, wherein said electrical links comprise at least one link forming an electrical return line configured to be common to all the optically stimulating modules of the probe, to which link said electronic unit of the optically stimulating module is connected.

3. The module as claimed in claim 1, wherein the electronic unit comprises the at least one substrate comprising two opposite faces, said two luminous diodes being mounted on a single one of the two faces of said substrate.

4. The module as claimed in claim 3, wherein the electronic unit comprises a suitable hermetic cover on the substrate.

5. The module as claimed in claim 3, wherein the electronic unit comprises a deposit produced by atomic layer deposition (ALD) covering the two luminous diodes.

6. The module as claimed in claim 1, wherein the at least one substrate comprises two substrates, on each of which one separate luminous diode is mounted.

7. The module as claimed in claim 1, wherein the casing comprises a ring that is closed at its two ends by two plugs, said two plugs bearing means for holding the electronic unit housed in the casing.

8. The module as claimed in claim 7, further comprising stimulating electrodes on the lateral surface of the ring.

9. The module as claimed in claim 1, further comprising a coating material injected into its casing around the hermetic electronic unit.

10. A probe that is implantable into a living being, said probe being configured to be electrically connected to an electrical power source and having an elongate architecture, wherein the probe comprises a plurality of optically stimulating modules juxtaposed along the probe and separated from each other by a non-zero distance, said probe comprising a coating material that fills a space between two adjacent modules, each module being the module as claimed in claim 1, said probe comprising a plurality of electrical paths each intended to be electrically connected, point-to-point, to one separate electrical path of the electrical power source, each optically stimulating module of the probe being connected in series on a separate electrical path of the probe via its dedicated electrical supply contact.

11. The probe as claimed in claim 10, further comprising a reinforcement formed of a wire over which said modules are slipped.

12. The probe as claimed in claim 11, wherein, between two adjacent optically stimulating modules, the probe comprises a mechanically dividing ring slipped over said reinforcement.

13. The probe as claimed in claim 10, further comprising an axially illuminating module located in proximity to a distal end of the probe.

14. An implantable illuminating device intended to be implanted into a living being with a view to locally illuminate a region of said living being, said device comprising an electrical power source comprising a plurality of parallel electrical supply paths and a probe that is electrically connected to the electrical power source and that has an elongate architecture between a proximal end and a distal end, wherein said probe of said device is the probe claimed in claim 10.

15. The device as claimed in claim 14, wherein the electrical power source is an implantable pulse generator.

16. An optically stimulating module to be integrated into a probe that is implantable into a living being with a view to locally illuminate a region of said living being, said probe being configured to comprise a chain formed from a plurality of these modules, wherein the module comprises:
 a casing,
 a hermetic electronic unit housed in said casing and comprising two luminous diodes connected back-to-back, and
 upstream electrical contacts, arranged on the casing and configured to connect to a first identical adjacent optically stimulating module located upstream in the chain of modules, and downstream electrical contacts, arranged on the casing and configured to connect to a second identical adjacent optically stimulating module located downstream in the chain,
 electrical links arranged between each upstream electrical contact and each downstream electrical contact, and
 a first dedicated electrical supply contact, arranged on its casing, to which its electronic unit is connected,
 wherein the casing comprises a ring that is closed at its two ends by two plugs, said two plugs bearing means for holding the electronic unit housed in the casing.

17. The module as claimed in claim 16, further comprising stimulating electrodes on the lateral surface of the ring.

18. A probe that is implantable into a living being, said probe being configured to be electrically connected to an electrical power source and having an elongate architecture, wherein the probe comprises a plurality of optically stimulating modules juxtaposed along the probe and separated from each other by a non-zero distance, said probe comprising a coating material that fills a space between two adjacent modules, each module being the module as claimed in claim 16, said probe comprising a plurality of electrical paths each intended to be electrically connected, point-to-point, to one separate electrical path of the electrical power source, each optically stimulating module of the probe being connected in series on a separate electrical path of the probe via its dedicated electrical supply contact.

19. The probe as claimed in claim 18, further comprising a reinforcement formed of a wire over which said modules are slipped.

20. The probe as claimed in claim 19, wherein, between two adjacent optically stimulating modules, the probe comprises a mechanically dividing ring slipped over said reinforcement.

21. An implantable illuminating device intended to be implanted into a living being with a view to locally illuminate a region of said living being, said device comprising an electrical power source comprising a plurality of parallel electrical supply paths and a probe that is electrically connected to the electrical power source and that has an elongate architecture between a proximal end and a distal end, wherein said probe of said device is the probe claimed in claim 18.

* * * * *